United States Patent [19]

Sievert et al.

[11] Patent Number: 5,447,685

[45] Date of Patent: Sep. 5, 1995

[54] MEDICAL WASTE DISPOSAL APPARATUS AND METHOD FOR DISPOSING OF WASTE

[75] Inventors: Michael K. Sievert, Cannon Falls; Curtis D. Luebke, Kenyon; Donald L. Sturtevant, Vadnais Heights, all of Minn.

[73] Assignee: Medivators, Inc., Cannon Falls, Minn.

[21] Appl. No.: 117,224

[22] Filed: Sep. 3, 1993

[51] Int. Cl.[6] .................. A61L 2/04; A61L 2/24
[52] U.S. Cl. ........................ 422/22; 422/307; 241/23; 241/65; 241/606
[58] Field of Search .......... 241/23, 65, 606, DIG. 38; 588/255; 422/22, 109, 307, 102; 432/262; 373/156

[56] References Cited

U.S. PATENT DOCUMENTS

| | | | |
|---|---|---|---|
| 1,710,234 | 4/1929 | Nelson | 432/262 X |
| 2,383,353 | 8/1945 | Steele | 432/262 X |
| 2,961,228 | 11/1960 | Moore | 422/102 X |
| 3,674,422 | 7/1972 | Gray | 422/307 |
| 3,699,906 | 10/1972 | Gallo | 110/185 X |
| 3,958,936 | 5/1976 | Knight, Jr. | 21/93 |
| 4,666,681 | 5/1987 | Ferrand et al. | 432/262 X |
| 4,860,958 | 8/1989 | Yerman | 241/23 |
| 4,905,916 | 3/1990 | Sorwick et al. | 241/23 |
| 4,984,748 | 1/1991 | Kimura | 241/65 |
| 4,992,217 | 2/1991 | Spinello | 422/307 X |
| 5,003,892 | 4/1991 | Bricken | 110/346 |
| 5,046,669 | 9/1991 | Wallace et al. | 241/23 |
| 5,166,488 | 11/1992 | Peppard | 241/65 X |
| 5,185,126 | 2/1993 | Adamski et al. | 422/109 X |
| 5,207,994 | 5/1993 | Suzuki et al. | 422/307 |
| 5,209,411 | 5/1993 | Dineley et al. | 241/17 |
| 5,213,758 | 5/1993 | Kawashima et al. | 422/307 X |

OTHER PUBLICATIONS

Sterimelt TM, Plastics Densification, 1992.
Spintech Inc.'s TAPS. Printed Aug. 1992.
American Delphi, Inc. and Environmental Disposal Systems, Inc. Announce Omega SDS The In-Office Sharps Disposal System.
Network International Medical Waste Management.
Introducing the MedAway-1 Waste Processor. The safer way to deal with medical waste disposal. Distributed by MedMark International. 1992 Medical Marketing International Inc.
Needle Destroyer. Fisher Scientific.
Infectious Waste Processing. A System For All Reasons. R. E. Baker Company, Inc.

Primary Examiner—Robert J. Warden
Assistant Examiner—E. Leigh Dawson
Attorney, Agent, or Firm—Merchant, Gould, Smith, Edell, Welter & Schmidt

[57] ABSTRACT

An industrial waste disposal apparatus which converts the waste from hazardous to nonhazardous form. The apparatus processes the waste into a solid block of nonhazardous material. The solid block may thereafter be disposed of through conventional disposal methods. This apparatus and process also reduces the volume up to 80% of the original volume.

30 Claims, 7 Drawing Sheets

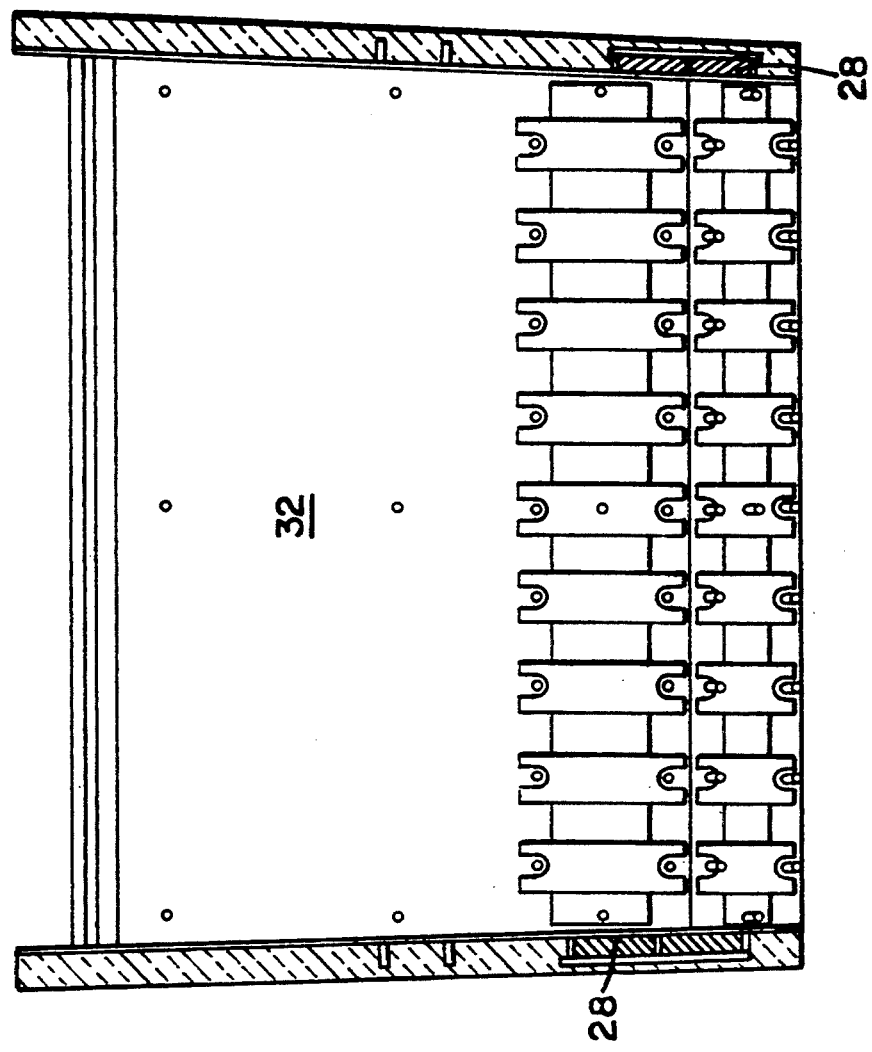
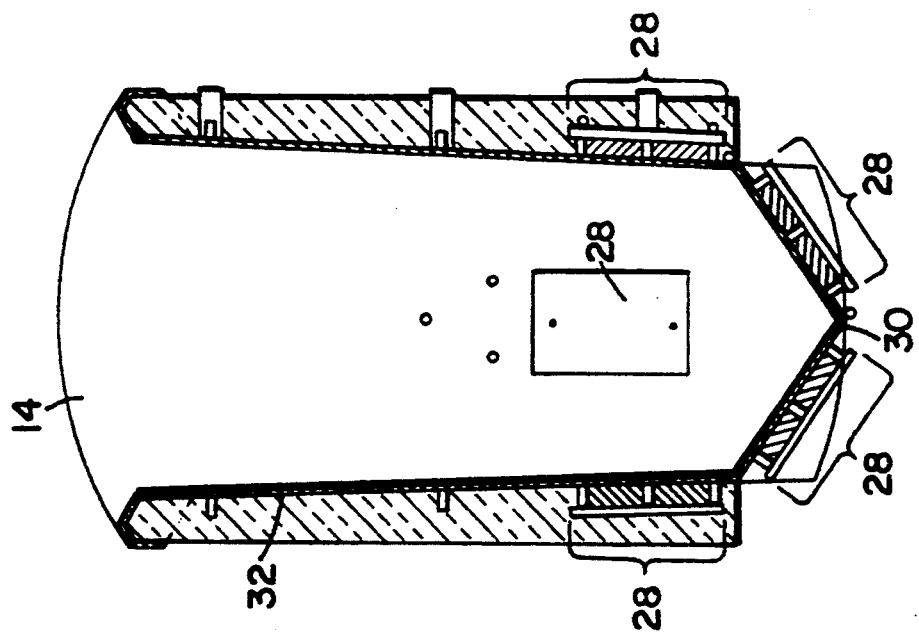

MEDICAL WASTE DISPOSAL APPARATUS AND METHOD FOR DISPOSING OF WASTE

FIELD OF THE INVENTION

The present invention relates generally to the field of devices employed to dispose of waste, in particular, medical waste such as syringes, surgical gowns, patient drapes, rigid plastics, and other waste generated which may or may not be contaminated.

BACKGROUND OF THE INVENTION

The safe disposal of medical waste presents a significant problem. Typically, in a hospital or medical facility, medical waste such as hypodermic needles, sharps collection devices, medical gowns, patient drapes, surgical drapes, Mayo stand covers, gauze, wound dressings, and other soiled articles must be disposed of safely. Untreated medical waste must be disposed of as hazardous waste, which is costly and burdensome. As a result of infectious diseases such as AIDS and other deadly diseases, the waste must be disposed of in hazardous waste sites. Oftentimes, the waste must be tracked and recorded also. Furthermore, the number of hazardous waste sites is limited and the capacity of such hazardous waste sites is continuously dwindling. Thus, there is a need for an improved method and apparatus for disposing of medical hazardous waste.

U.S. Pat. Nos. 5,046,669 and 4,905,916 disclose syringe disposal apparatuses. In one embodiment, the apparatus collects used syringes, grinds up the syringes, and melts the syringes into a solid puck of plastic, wherein the needles are encapsulated therein. However, such an apparatus is limited to syringes and other small objects and thus there is a need for an apparatus to accept all forms of industrial waste including medical waste.

U.S. Pat. No. 5,228,271 relates to a collection device for medical gowns and other soft goods. However, this patent does not address the need to convert the waste material from a hazardous form to a non-hazardous form. Thus, there is a need for an apparatus to collect all forms of medical waste and convert the medical waste to a safe form which may be disposed of readily and easily.

SUMMARY OF THE INVENTION

The present invention relates to an apparatus and method for disposing of industrial waste material, in particular, medical waste. The apparatus comprises:
(a) a crucible for receiving the waste;
(b) a heating means for heating the crucible;
(c) a means for controlling the heating means, the controlling means selectively activating the heating means to heat the crucible and the waste material therein to a temperature above the melting point of substantially all of the waste contained therein, and thereafter deactivating the heating means to allow the crucible and the contents therein to cool to a temperature below the melting point thereby producing a block of material;
(d) a means for removing the block of material from the crucible; and
(e) a receptacle to receive the block of material.

The present invention provides for an improved apparatus and method for the disposal of industrial waste, particularly medical waste. It utilizes an economical, portable device which renders hazardous material non-hazardous and provides short cycle times for use in busy hospital environments. It will be further appreciated that a need exists for a method for disposing of such industrial waste. The present invention also offers further advantages over the prior art, and solves other problems associated therewith.

The above described features and advantages along with various other advantages and features of novelty are pointed out with particularity in the claims of the present application. However, for a better understanding of the invention, its advantages and objects attained by its use, reference should be made to the drawings which form a further part of the present application into the accompanying descriptive matter in which there is illustrated and described preferred embodiments of the present invention.

A BRIEF DESCRIPTION OF THE DRAWINGS

FIG. 7 is a sectional side view of the crucible of the present invention.

FIG. 8 is an end view of the crucible of the present invention.

DETAILED DESCRIPTION OF THE INVENTION

The present invention provides a compact, safe, and economical apparatus and method for disposing of industrial waste. The present invention is directed toward an apparatus which receives industrial waste, renders the waste non-hazardous and also compacts the waste into a solid block, in a short period of time, and thereafter deposits the block in a receptacle to be removed at a later period of time.

Figure 1:
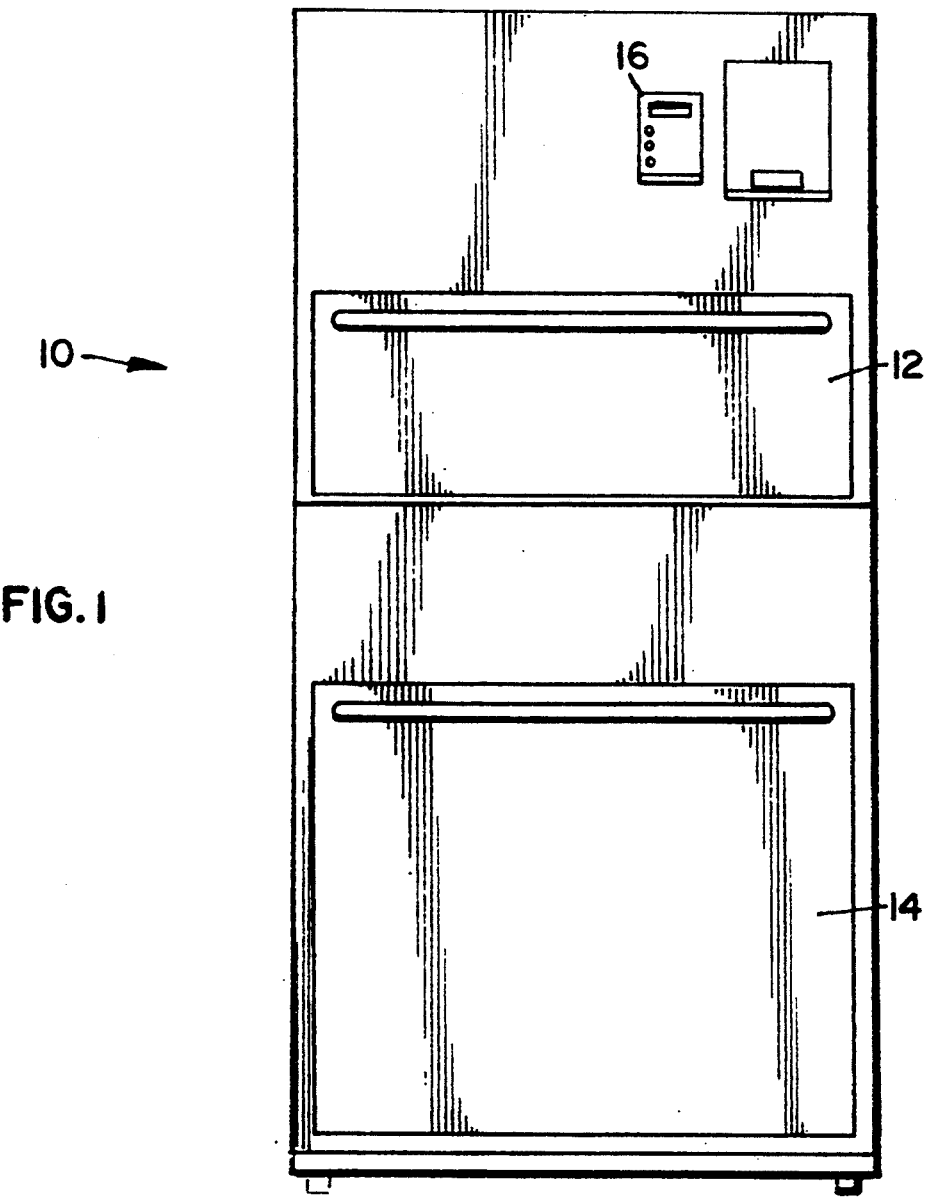
FIG. 1 is a frontal view of the apparatus of the present invention.

FIG. 1 illustrates a frontal view of apparatus 10 of the present invention. Generally, the apparatus 10 and its features is microprocessor controlled. The apparatus 10 has a top loading door 12, a bottom receptacle door 14 and a control panel 16. Apparatus 10 is preferably a portable unit which can be moved easily on wheels. In a hospital environment, the apparatus 10 may be moved to different locations. The preferred location is a room or area where waste is now collected. The machine can then be vented outside or into the existing exhaust venting system. Examples of waste which may be deposited in the present invention include materials that are made of polypropylene or polyethylene i.e., (syringe barrels, syringe needles, medical gowns and drapes, Mayo stand covers, gauze, wound dressings, emesis cups, bedpans, wash basins and other waste).

The waste material is deposited in apparatus 10 through top door 12. The material is heated, sterilized, compacted and deposited at the bottom of apparatus 10. The material is thereafter removed through door 14. The operation is directed by the operator through control panel 16. Control panel 16 provides a means whereby data may be entered or read during the operation.

Figure 2:
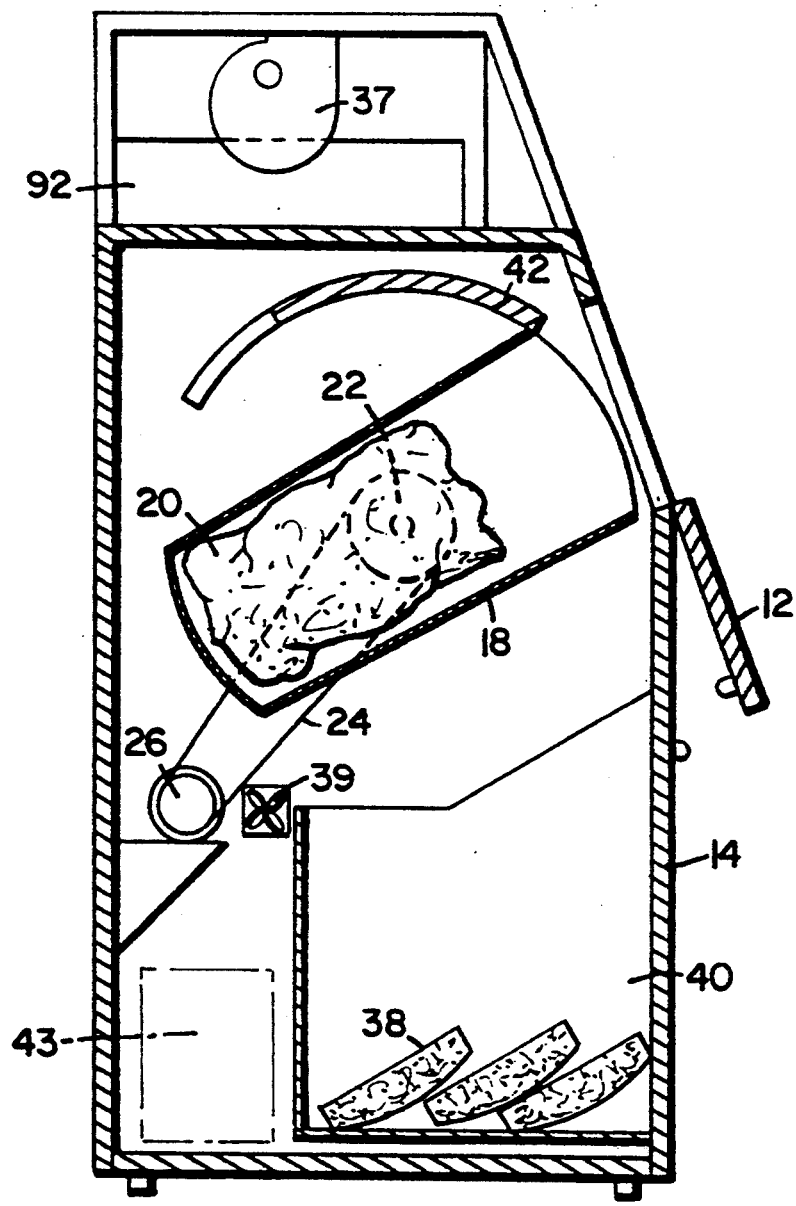
FIG. 2 is a sectional side view of the apparatus of the present invention in a loading mode.

FIG. 2 is a side view of FIG. 1, with the side panel of apparatus 10 removed. FIG. 2 illustrates crucible 18 in a load mode. With door 12 being opened, (it is shown closed in FIG. 3), crucible 18 can be loaded with waste material, which is shown as 20. Crucible 18 is rotatably engaged through pulley wheel 22, chain 24 and drive gear 26. When the operator intends that the waste 20 be processed, control panel 16 is employed. The operator closes door 12, and enters the appropriate key pad combination of control panel 16, which thereafter rotates crucible 18 to a heating mode, which is illustrated in FIG. 4. The crucible is rotated by a motor which turns drive gear 26, thereby rotating crucible 18. Although the preferred method of preparing the crucible 18 for heating is by rotating the crucible's opening away from door 12, the key is that the crucible 18 be heated and covered. It is not necessary to rotate the crucible 18 prior to heating.

The crucible 18 can be heated up in numerous ways. As shown in FIGS. 7 and 8, in the preferred embodiment, the heating elements are situated around the bottom of crucible 18. The heating elements are generally referred to as 28 in FIG. 7 and are located on both ends, both sides, and on the "V" shaped bottom. In the preferred embodiment, the heaters are MICA strip heaters commercially available from Tempco. There are a total of six heaters used for a total wattage of 9500 W. Panel 42 is insulated which prevents the external surface of apparatus 10 from getting too hot. During heating, large amounts of heat are generated. For safety and comfort reasons, it is preferred to minimize the heat flow to the exterior surfaces. This is accomplished through known methods of heat dissipation and absorption. For example, both the apparatus and crucible may be insulated with commercially available insulation.

Figure 3:
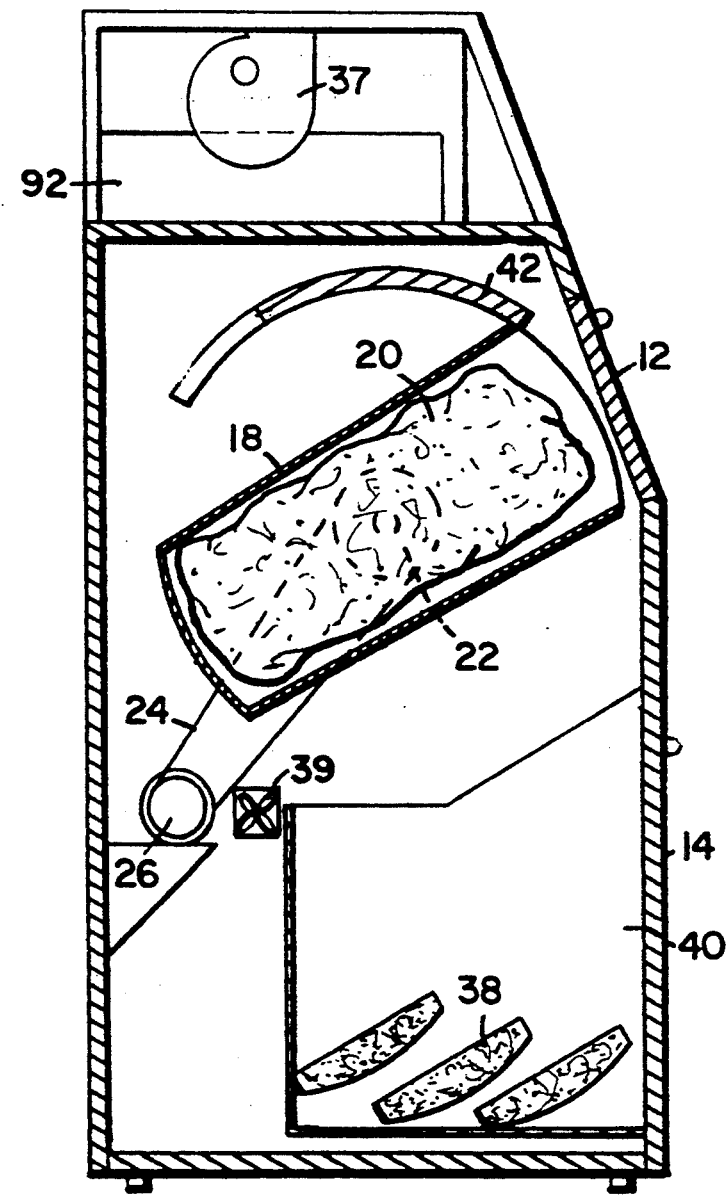
FIG. 3 is a sectional side view of the apparatus of the present invention in a loaded mode.
Figure 4:
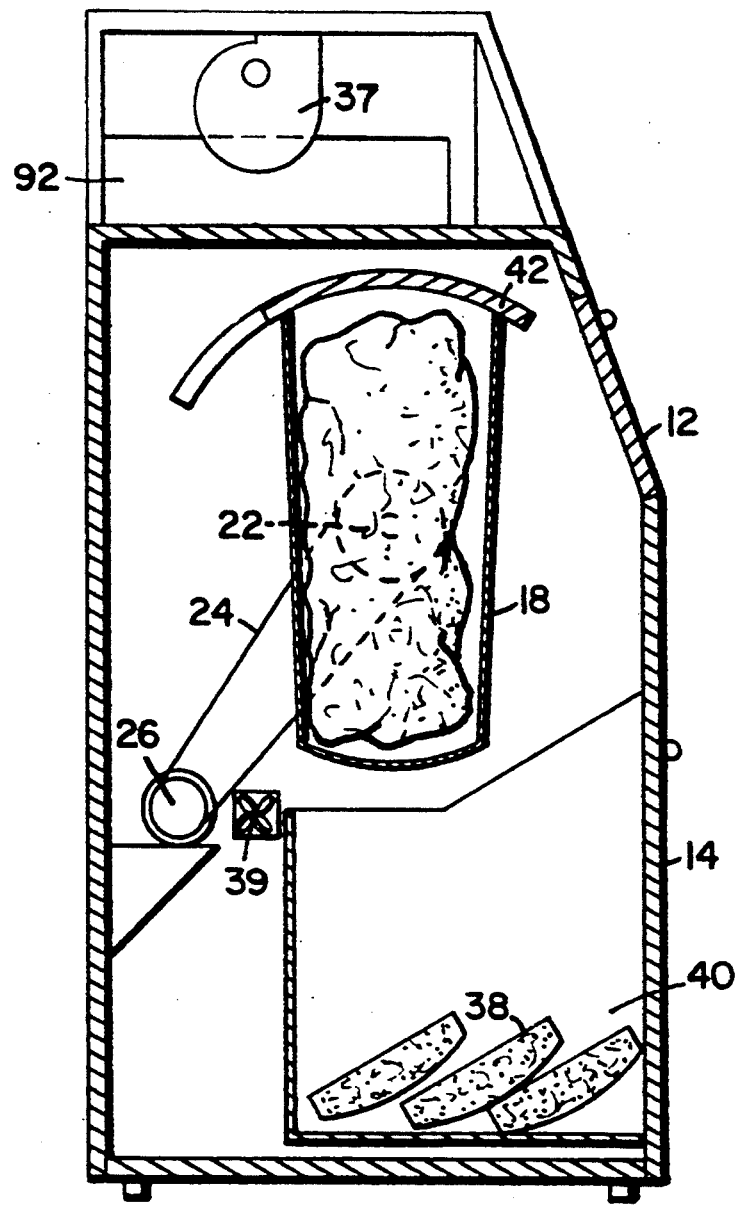
FIG. 4 is a sectional side view of the apparatus of the present invention in a heating mode.
Figure 5:
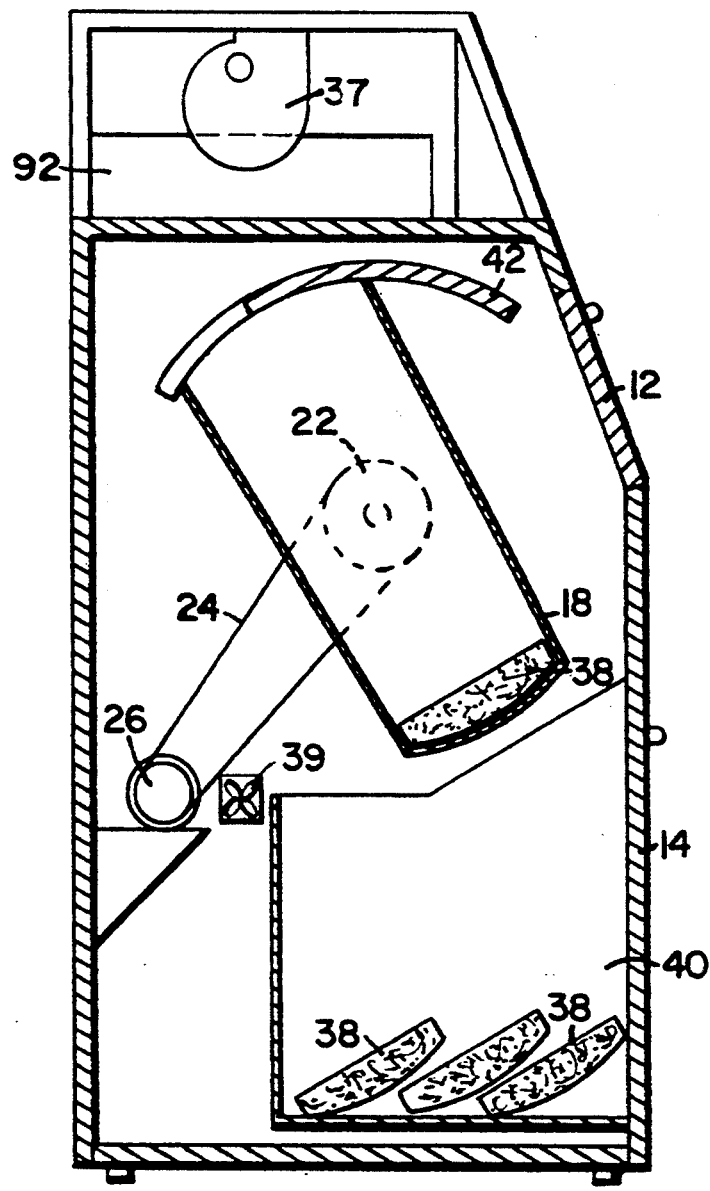
FIG. 5 is a sectional side view of the apparatus of the present invention at the final cooling mode.

The crucible is shown in FIGS. 2–6 as 18 and is the vessel whereby the industrial waste 20 is heated and compacted. Preferably, the walls of the crucible 18, 30 and 32 as shown as in FIG. 7, are not parallel, but rather are angled slightly outwardly, such that the block of waste material 20 at the bottom may easily fall out upon rotation of the crucible 18 in an inverted position. Preferably, the angle of the walls should be angled approximately 2°. Preferably, the bottom of crucible is curved or in a V-shape. A curved bottom crucible is shown in FIGS. 2–4 with a V-shaped crucible shown in FIG. 5. Preferably, the crucible is V-shaped. The V-shaped results in an easier release of the block 38 from the crucible 18. The V-shape allows a better concentration of the heat into the waste material put in the crucible.

In the preferred embodiment, the crucible is made of 0.125 inch thick 6061 aluminum. The interior of the crucible is lined with TEFLON ® or any other non-stick coating, which provides for an easy release of the block of waste 38. The top of the crucible (opposite the bottom) has rolled edges which add stiffness and rigidity to the long edge of the crucible.

FIG. 4 illustrates the heating mode of the present apparatus after the material 20 has been deposited in the crucible 18. Crucible 18 is rotated to the position shown in FIG. 4. The crucible 18 is then heated to a temperature which is preset such that it sufficiently melts the industrial waste 20 in the crucible 18. Typically, in a hospital setting, there is a significant amount of polypropylene which is generated as waste material. The melting point of polypropylene is about 330°–360° F. Thus to ensure proper melting of the polypropylene, the internal crucible temperature should be above 380°–400° F., preferably about 450°–480° F. This crucible temperature should be maintained for approximately 30 minutes to ensure full melting and sterilization of the material. Obviously, if the industrial waste which is to processed within the present invention has a melting point higher or lower than this, the temperature presets and/or the processing time may be adjusted accordingly. The only requirement is that the temperature and period at which the temperature is held is sufficient such that substantially all of the waste becomes molten, such that it can collect at the bottom of the crucible 18.

Typically, during the heating process, gases and smoke are generated which are contained by the cover 42. Thereafter, the gases can be circulated and vented out of the area in any common known method.

An alternate method to construction and cooling of the crucible would be to cast the crucible out of aluminum. The cast crucible could have internal or external ducts which have a cooling fluid pumped thereby eliminating the need for the blowers that are used for cooling in the preferred embodiment. The preferred blowers are 100 cubic feet per minute blowers. A HEPA filter is also used. If the cooling fluids were used, the blowers could be down sized to handle just the smoke and gases produced by the melting of the plastic.

The following is a description of the preferred embodiment. After the required heat time the heaters 28 turn off. The crucible 18 remains in the upright heat position under the cover 42. The lower cooling fan 39 turns on, thus drawing air from outside the cabinet at approximately 100 cubic feet per minute. The incoming air is directed at the bottom of the crucible 18. At the same time blower 37 turns on. This blower, draws air from the cabinet through a 18×24 HEPA filter 92 commercially available from Donaldson at approximately 300 cubic feet per minute thereby creating a negative pressure in the cabinet.

The crucible 18 remains in the upright position until the crucible 18 temperature reaches 350° F. At that time the crucible moves to the cool position. In the cool position, openings in the cover 42 allow any remaining smoke and gases to be exhausted from the inside of the crucible 18. Also, in this position a third blower 94 turns on. This blower 94 is bringing in approximately 100 cubic feet per minute of out of cabinet air. The air blower is connected to the cover 42 by a flexible duct. This blower is blowing air into the crucible 18 to solidify the top surface of the melted brick, thereby allowing the brick to be dropped into the drawer before the entire brick has solidified.

The crucible 18 remains in the cool position until the temperature of the crucible has been lowered to about 190° F. to 150° F. This temperature is determined by the temperature required to allow the brick to dump from the crucible 18.

Figure 6:
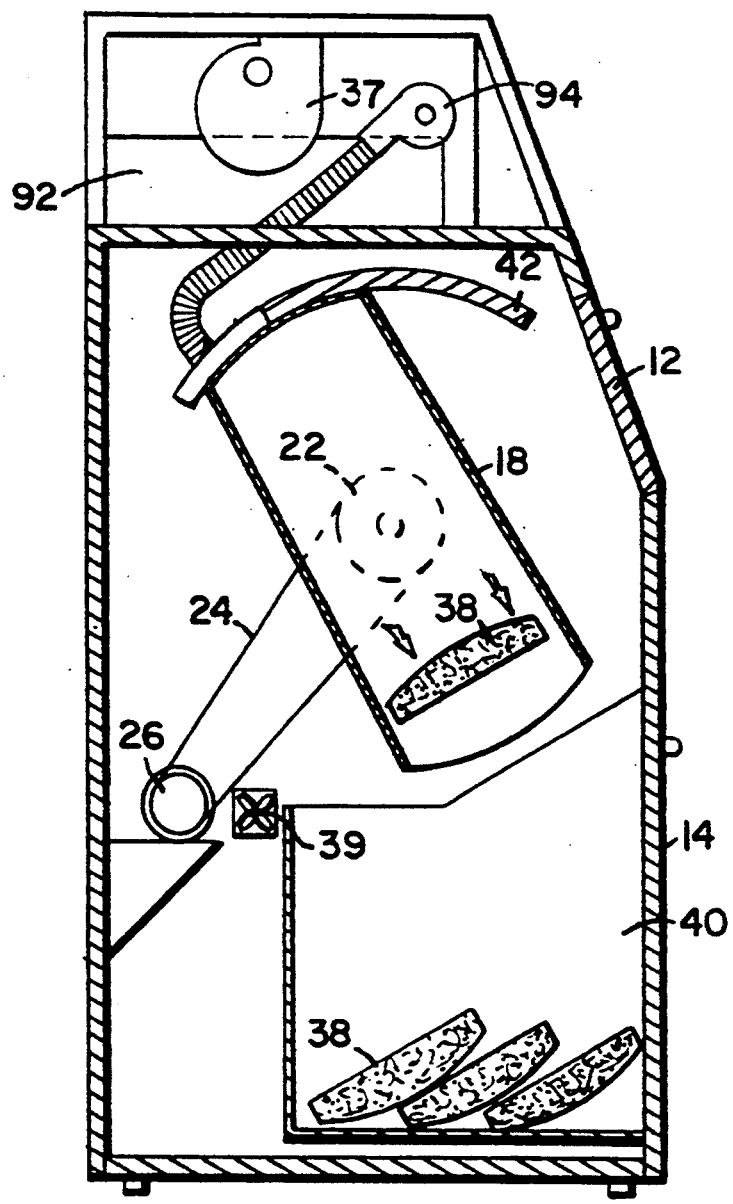
FIG. 6 is a sectional side view of the apparatus of the present invention in the dumping mode.

After the block 38 is sufficiently cooled, the crucible 18 is again rotated, as shown in FIG. 6, with the block 38 leaving the crucible 18 and collecting at the bottom of the receptacle 40. The blocks can be thereafter collected by opening door 14 and removing the blocks. With regard to medical waste, because of the temperature of the preferred embodiment exceeding 500° F., the waste material is converted from hazardous waste to non-hazardous waste. Thus, the block may be disposed of in any landfill site, and does not need to be tracked, as required under federal law for hazardous waste.

Regarding the motor 26, chain 24 and sprockets 22 preferably the motor is sized to handle the inertial load and torque require to rotate the crucible 18 with a full load from the cool position to the dump position. The motor in the preferred embodiment is a p/n 4CSMGK-101 motor commercially available from oriental motor with a 90:1 gear box p/n 4GK90KA and a 2 to 1 sprocket chain drive.

Referring to FIG. 2, item 43 is a vacuum pump which could be used with a separate waste bag connected to a vacuum port. By using the vacuum pump on the waste bag, the waste bag could be reduced in volume, inserted in crucible 18 and thus more waste could be put in the crucible 18. A waste bag is described in U.S. Pat. No. 5,228,271.

The doors 12 and 14, in the preferred embodiment, have sensors and locks operating cooperatively. When the crucible 18 is in the heating, cooling and dump mode, automatic door locks prevent an operator from opening door 12 or drawer 14, which could result in a safety hazard. Furthermore, in the preferred embodiment, when crucible 18 is dumping the block into receptacle 40, if block 38 is still hot, door 14 may be locked as well. The sensors which control the locking and unlocking of the doors may be temperature sensors located on the crucible or other types of sensors known in the art. The locks and sensors used in the preferred embodiment are as follows: A tab on the door 12 or drawer 14 depresses the actuator on a microswitch thereby sending a signal to the microprocessor that the 12 door or drawer 14 is in the closed position. After the closed position has been met the current to a solenoid holding a spring loaded plunger is released. The plunger moves forward through a hole in the door 12 or drawer 14 tab thereby locking the door 12 or drawer 14.

If power to the unit is lost all doors and drawers remain locked. When power to the unit is regained the microprocessor checks the temperature of the crucible 18, if the temperature is not below the safe door opening temperature the crucible 18 will rotate to the cool position and will remain in that position until the safe temperature is reached at which time the crucible 18 will rotate to the load position and the door 12 and drawer 14 will unlock.

An alternative embodiment utilizes a plurality of crucibles. The crucibles are attached in series to a continuous loop conveyor system. When one crucible is filled with waste material, the operator rotates a new crucible in a loading position. The crucibles that are filled and rotated away from the loading door are heated at some position in the loop. Thereafter the crucible is cooled and is inverted or manipulated in some manner to release the cooled block of material. Thereafter, the empty crucible is eventually rotated back into position to be loaded. This embodiment provides for a continuous receptacle being available for waste with no down time. The number of crucibles can range from two or greater. The apparatus must be modified to insulate the loading door area from the heating which could be occurring concurrently in the apparatus. The safety features and control panel features described herein could be employed with this embodiment. The safety features would include the following: the loading door would be locked when the movement of the crucibles occurs. A temperature of the crucible would be detected and the system would not allow the advancement of the crucibles until the required next time and temperature were achieved.

Control panel 16 provides the operator with the ability to monitor and control the apparatus. The display on the control panel can monitor a variety of things, such as where in the cycle the apparatus is at, the temperature of the crucible, as well as instructions to the operator. In the preferred embodiment, plastic medical waste is placed in the crucible through the loading door. When the operator presses a start button, the doors are locked and the crucible is driven to its position for heating. After the waste has been heated to approximately 500° F. for a minimum of 30 minutes, it is melted into a block. The crucible is then rotated to a cooling position where one or more fans cool the crucible and exhaust any gases through a filter. When the crucible is sufficiently cool, it is rotated to the dump position where the block is dumped into the receiving bin for safe disposal thereafter. The control panel may provide an output for all of the above. The control panel also retains operating information, such that at a later time, an operator can download the system to determine data such as operating temperatures time, date and ID number that have occurred in the past. This is essential in the preferred embodiment, to ensure that correct temperatures have always been obtained, such that materials are rendered non-hazardous. In one embodiment, a sensor is installed which triggers a warning system, such that if the preset temperature is not reached, the operator is notified. The predetermined time which is required to melt the waste is maintained only when the preset temperature is held. Thus, when temperatures go below the pre-set temperature, the time is held until the pre-set temperature is achieved. If the temperature is never achieved, an error code is given and the cycle is aborted.

A printout of the downloaded system may be accessed through a printer which can be attached to the apparatus. In the preferred embodiment, the operator control panel has sealed controls to avoid problems resulting from dirt or the environment. Output drivers from the control panel are directed to controlled door locks, cooling fans, crucible heaters and the drive motor. In the preferred embodiment the electronics package has individual output drivers which are easily removed and replaced. The external wiring is connected through prewired screw terminals that slide into pin headers. The microprocessor circuit and output drivers are on separate boards to improve isolation and serviceability and all outputs utilize industry standard optically isolated modules.

In the preferred embodiment, during every heat/cool cycle, a number of conditions are monitored for abnormal conditions. If any of these conditions are detected, the system will halt and display the error. A red light may also be illuminated. The system will restart upon command and run through the entire cycle. In the preferred embodiment, the crucible position is monitored by several position sensors. If, during any crucible movement, the sensors detector an out of sequence or invalid position, an error is signaled and error handling positions are enacted. In this case, progress may be hampered by an overloaded crucible, jammed crucible or motor problems which result in faulty sensing.

With regard to the heaters, when the crucible is in the heat position, the crucible heaters are thereafter activated. The temperatures are monitored by two sensors mounted on the crucible. Each sensor is placed physically close to its associated heater strip. The heaters are placed in two zones. Zone 1 are end heaters and bottom heaters. Zone 2 are the two side heaters. Control of each zone is independent. Heaters are placed on the side and the bottom of the crucible. The upper heater is used as an axillary heater to assist the lower heater. In addition, an error condition will be signaled to indicate whether the failure is related to the heaters, heat drive circuitry or the sensors themselves. If progress to operating temperature is not sufficient, or if the temperature is increasing while the heaters are suppose to be off, an error will be signaled. The exhaust fan may be activated during portions of the heat option to keep the cabinet temperature to a minimum. Upon completion of the heat operation, the fans are turned on, the motor drives a crucible to the cool position, the upper fan exhausts hot air from inside the crucible through a filter and into the room or ducted outside or into the central exhaust system. The optional lower fans blow ambient air from outside the cabinet into the bottom of the crucible. When the crucible has cooled to the target temperature, the cooling cycle is complete. If the cycle is not completed within a prescribed period, an error signal will be noted, and the system will abort the cycle.

Possible system errors and warnings are incorporated in the preferred embodiment. An example is, if the system detects that more than 1.5 hours is required to achieve the preset temperature, or more than 3 hours is required for the entire cycle, a time error will be evoked and the system will be halted. The reasoning is that the time should not exceed this limit and either something is broken (motor, fan, heater, etc.) or the operator paused the system and left the vicinity, potentially leaving the temperature at a very high level for a very extended duration. Other fault conditions include: (i) heat, the average of the upper and lower temperatures exceed the maximum over said point tolerance or while the system is idle and the crucible is at the load position the average temperature exceeds the maximum safe temperature for opening the door by more than 25° F.; (ii) temperature, the difference between the reading and the upper and lower temperatures exceeds the maximum allowed deviation period position; (iii) an invalid or out of sequence position has been detected; and (iv) door, either the dump bin or load door sensors report an open door when the door locks are engaged. Other warning systems may also be incorporated.

It will be understood that even though these numerous characteristics and advantages of the invention have been sent forth in the foregoing description, together with details of the structure and function of the invention, the disclosures illustrative only, and changes may be made in detail, especially matters of shape, size and arrangement of the parts or in a sequence or the timing of the steps, within the broad principle of the present invention, to the full extent indicated by the broad general meaning of the terms in which the appended claims are expressed.

We claim:

1. An apparatus for disposal of waste material, said apparatus comprising:
    (a) a crucible operatively configured to receive unprocessed waste material, said crucible being rotatable about a horizontal axis;
    (b) a means for rotating said crucible;
    (c) a heating means for heating said crucible;
    (d) a means for controlling said heating means and said rotating means, wherein said controlling means includes:
        (i) means for activating said rotating means to rotate said crucible to a heating position,
        (ii) means for activating said heating means to heat said crucible to a temperature above the melting point of substantially any waste material contained in said crucible until the waste material is fully melted and sterilized,
        (iv) means for activating said rotating means to rotate said crucible to a cooling position to allow said crucible and any waste material contained therein to cool to a temperature below said melting point to produce a disposable block of waste material, and
        (v) means for activating said rotating means to rotate said crucible to a dumping position such that the block of waste material drops out of said crucible; and
    (e) a receptacle operatively configured to receive said block of material when said crucible is rotated to the dumping position.

2. The apparatus of claim 1 wherein said crucible has side walls which are spaced apart and angled outwardly at an angle with respect to one another.

3. The crucible of claim 2 wherein the angle between said side walls is approximately two degrees.

4. The apparatus of claim 1 wherein said crucible has a bottom portion, said bottom portion including first and second generally planar portions, said first and second portions operatively connected along an edge and extending away from said edge at an angle from one another.

5. The apparatus of claim 1 wherein said heating means comprise a plurality of heating elements situated on the exterior of said crucible.

6. The apparatus of claim 1 wherein said controlling means monitors said heating means to maintain a temperature of about 500°–550° F. for about forty minutes.

7. The apparatus of claim 1 wherein said controlling means reheats said crucible for a set period of time if the temperature drops below a preset temperature.

8. The apparatus of claim 1, further comprising:
    (a) at least one door for accessing said apparatus, and
    (b) a means for locking said door automatically when the temperature of said crucible is above a preset temperature.

9. The crucible of claim 1 further comprising a first cooling fan for directing a flow of air from outside of said apparatus onto the crucible to cool the block of waste material.

10. The apparatus of claim 9 further comprising a second cooling fan and a filter disposed between said second cooling fan and said crucible, wherein said second cooling fan is configured to generate an air flow through said filter and out of said apparatus which is greater than the air flow provided by said first cooling fan into said apparatus; whereby negative pressure is generated in said apparatus.

11. The apparatus of claim 1 further comprising an operator control panel, said panel having displays selected from the group consisting of time remaining, temperature, printout symbol, and combinations thereof.

12. The apparatus of claim 1 having data storage capabilities for the storage and printing of operating information.

13. The apparatus of claim 1 wherein said crucible includes a bottom portion which is generally concave with respect to an open end of said crucible to facilitate removal of the block of waste material from said crucible, 14. The apparatus of claim 1 wherein said controlling means is configured to actuate said rotating means to initially rotate said crucible to a loading position to provide an operator with access to an opening in said crucible such that unprocessed waste material may be placed directly in said crucible, 15. The apparatus of claim 1 further comprising a fixed cover configured to substantially seal an opening in said crucible when said crucible is in the heating position, and wherein said fixed cover includes an opening configured to release any smoke and gas disposed in said crucible when said crucible is in the cooling position, 16. The apparatus of claim 15 further comprising a cooling fan arranged to direct a flow of air against the block of waste material when said crucible is in the cooling position to solidify an exposed surface of the block; whereby the block of waste material may be dropped from said crucible before all of the waste material in the block has solidified.

17. A method for processing waste material to facilitate the disposal of the waste material, said method comprising the following steps:
   (a) placing unprocessed waste material directly in a crucible
   (b) heating the crucible and the waste material therein to a temperature above the melting point of substantially all of the waste material until the waste material is fully melted and sterilized;
   (c) cooling the crucible to allow the waste material to cool to a temperature below said melting point to produce a block of waste material wherein the cooling step comprises the step of rotating the crucible from the heating position to a cooling position;
   (d) rotating the crucible about a horizontal axis into a substantially inverted dumping position; and
   (e) dropping the block of waste material into a receptacle, wherein the block of waste material is suitable for direct disposal without further processing.

18. The method of claim 17 wherein the crucible has side walls which are spaced apart and angled outwardly at an angle with respect to one another.

19. The method of claim 18 wherein the angle between the side walls is approximately two degrees.

20. The method of claim 17 wherein the crucible has a bottom portion, the bottom portion including first and second generally planar portions, the first and second portions operatively connected along an edge and extending away from the edge at an angle from one another.

21. The method of claim 17 wherein said heating step comprises heating a plurality of heating elements situated on the exterior of the crucible.

22. The method of claim 17 wherein said heating step comprises maintaining a temperature in the crucible of about 500°–550° F. for about forty minutes.

23. The method of claim 17 wherein said heating step comprises reheating the crucible for a set period of time if the temperature drops below a preset temperature.

24. The method of claim 17, wherein the crucible and receptacle are accessed by at least one door, and wherein said method further comprises the step of locking the door automatically when the temperature of the crucible is above a preset temperature, 25. The method of claim 17 wherein said cooling step comprises actuating cooling fans to cool the crucible and the waste material therein, 26. The method of claim 17 further comprising an operator control panel, said panel having displays selected from the group consisting of time remaining, temperature, printout symbol, and combinations thereof.

27. The method of claim 17 having data storage capabilities for the storage and printing of operating information.

28. The method of claim 17 wherein the crucible includes a bottom portion which is generally concave with respect to an open end of the crucible to facilitate removal of the block of waste material from the crucible during the dropping step.

29. The method of claim 17 wherein the heating step comprises the step of sealing the crucible while the crucible is being heated, and wherein the cooling step comprises the step of unsealing the crucible during cooling to release any smoke and gas disposed in the crucible.

30. The method of claim 17 wherein the cooling step comprises the step of directing a flow of air against the block of waste material when the crucible is in the cooling position to solidify an exposed surface of the block; whereby the block of waste material may be dropped from the crucible before all of the waste material in the block has solidified.

* * * * *

UNITED STATES PATENT AND TRADEMARK OFFICE
CERTIFICATE OF CORRECTION

PATENT NO. : 5,447,685

DATED : September 5, 1995

INVENTOR(S) : Sievert et al.

It is certified that error appears in the above-identified patent and that said Letters Patent is hereby corrected as shown below:

On column 3, line 46, please insert --the-- after the word "of"

On column 5, line 3, please delete "require" and substitute therefore --required--

On column 5, line 31, please delete "12 door" and substitute therefore --door 12--

On column 5, line 6, please delete "oriental motor" and substitute therefore --Oriental Motor--

On column 6, line 58, please delete "detector" and substitute therefore --detect--

Signed and Sealed this

Fifth Day of December, 1995

Attest:

BRUCE LEHMAN

Attesting Officer

Commissioner of Patents and Trademarks